US011883080B1

United States Patent
Krawiec et al.

(10) Patent No.: US 11,883,080 B1
(45) Date of Patent: Jan. 30, 2024

(54) REVERSE DYNAMIZATION IMPLANTS

(71) Applicant: GLOBUS MEDICAL, INC., Audubon, PA (US)

(72) Inventors: Catherine Krawiec, Conshohocken, PA (US); Peter Evans, Lafayette Hill, PA (US); Chad Glerum, Pennsburg, PA (US)

(73) Assignee: Globus Medical, Inc, Audubon, PA (US)

( * ) Notice: Subject to any disclaimer, the term of this patent is extended or adjusted under 35 U.S.C. 154(b) by 0 days.

(21) Appl. No.: 17/812,257

(22) Filed: Jul. 13, 2022

(51) Int. Cl.
*A61F 2/44* (2006.01)
*A61B 17/72* (2006.01)

(52) U.S. Cl.
CPC ...... *A61B 17/7233* (2013.01); *A61B 17/7208* (2013.01); *A61B 17/7225* (2013.01)

(58) Field of Classification Search
CPC .......... A61F 2/44–447; A61F 2/4611
See application file for complete search history.

(56) References Cited

U.S. PATENT DOCUMENTS

| 4,349,921 A | 9/1982 | Kuntz |
| 4,599,086 A | 7/1986 | Doty |
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 5,681,872 A * | 10/1997 | Erbe ............ A61L 27/025 106/35 |
| 6,039,761 A | 3/2000 | Li et al. |
| 6,045,579 A | 4/2000 | Hochschuler et al. |
| 6,080,193 A | 6/2000 | Hochschuler et al. |
| 6,099,531 A | 8/2000 | Bonutti |

(Continued)

FOREIGN PATENT DOCUMENTS

| CA | 2088066 A1 | 1/1992 | |
| CN | 102510745 A * | 6/2012 | ............. A61F 2/447 |

(Continued)

*Primary Examiner* — Eduardo C Robert
*Assistant Examiner* — Steven J Cotroneo

(57) ABSTRACT

Implants, systems, and methods of reverse dynamization. The implants, such as expandable spinal implants, bone plates, and intramedullary nails, are securable to bone. The implant may have a moveable component creating a semi-rigid configuration to allow for micro-motion of the bone for a period of time. The moveable component is changeable, for example, based on material properties, change of state, or mechanical or electrical operation, to a static condition creating a rigid configuration to prevent subsequent movement of the bone. The reverse dynamization implants may be used to accelerate bone healing and obtain superior bone fracture healing.

13 Claims, 11 Drawing Sheets

(56) References Cited

U.S. PATENT DOCUMENTS

| | | | |
|---|---|---|---|
| 6,126,689 A | 10/2000 | Brett | |
| 6,176,882 B1 | 1/2001 | Biedermann et al. | |
| 6,258,125 B1 | 7/2001 | Paul et al. | |
| 6,558,423 B1 | 5/2003 | Michelson | |
| 6,562,074 B2 | 5/2003 | Gerbec et al. | |
| 6,576,016 B1 | 6/2003 | Hochschuler et al. | |
| 6,554,863 B2 | 8/2003 | Paul et al. | |
| 6,641,614 B1 | 11/2003 | Wagner et al. | |
| 6,648,917 B2 | 11/2003 | Gerbec et al. | |
| 6,666,891 B2 | 12/2003 | Boehm, Jr. et al. | |
| 6,692,495 B1 * | 2/2004 | Zacouto | A61F 2/4425 606/279 |
| 6,706,070 B1 | 3/2004 | Wagner et al. | |
| 6,752,832 B2 | 6/2004 | Ulrich | |
| 6,814,756 B1 | 11/2004 | Michelson | |
| 6,830,589 B2 | 12/2004 | Erickson | |
| 6,849,093 B2 | 2/2005 | Michelson | |
| 6,852,129 B2 | 2/2005 | Gerbec et al. | |
| 6,863,673 B2 | 3/2005 | Gerbec et al. | |
| 6,881,228 B2 | 4/2005 | Zdeblick et al. | |
| 7,018,415 B1 | 3/2006 | McKay | |
| 7,070,598 B2 | 7/2006 | Lim et al. | |
| 7,204,853 B2 | 4/2007 | Gordon | |
| 7,217,291 B2 | 5/2007 | Zucherman et al. | |
| 7,282,063 B2 | 10/2007 | Cohen et al. | |
| 7,316,714 B2 | 1/2008 | Gordon | |
| 7,473,276 B2 | 1/2009 | Aebi et al. | |
| 7,547,325 B2 | 6/2009 | Biedermann et al. | |
| 7,621,953 B2 | 11/2009 | Braddock, Jr. et al. | |
| 7,641,693 B2 | 1/2010 | Gutlin et al. | |
| 7,682,396 B2 | 3/2010 | Beaurain et al. | |
| 7,749,270 B2 | 7/2010 | Peterman | |
| 7,753,958 B2 | 7/2010 | Gordon | |
| 7,771,473 B2 | 8/2010 | Thramann | |
| 7,780,732 B2 | 8/2010 | Abernathie | |
| 7,799,081 B2 | 9/2010 | McKinley | |
| 7,815,683 B2 | 10/2010 | Melkent et al. | |
| 7,837,734 B2 | 11/2010 | Zucherman et al. | |
| 7,875,078 B2 | 1/2011 | Wysocki et al. | |
| 7,901,409 B2 | 3/2011 | Canaveral et al. | |
| 7,909,869 B2 | 3/2011 | Gordon | |
| 7,951,199 B2 | 5/2011 | Miller | |
| 7,985,256 B2 | 7/2011 | Grotz et al. | |
| 8,062,375 B2 | 11/2011 | Glerum | |
| 8,070,813 B2 | 12/2011 | Grotz et al. | |
| 8,123,810 B2 | 2/2012 | Gordon | |
| 8,137,405 B2 | 3/2012 | Kostuik et al. | |
| 8,172,902 B2 * | 5/2012 | Kapitan | A61F 2/4611 623/17.14 |
| 8,192,495 B2 | 6/2012 | Simpson et al. | |
| 8,303,663 B2 | 11/2012 | Jimenez et al. | |
| 8,377,140 B2 | 2/2013 | DeFalco et al. | |
| 8,394,129 B2 | 3/2013 | Lopez et al. | |
| 8,394,143 B2 | 3/2013 | Grotz et al. | |
| 8,435,296 B2 | 5/2013 | Kadaba et al. | |
| 8,454,695 B2 | 6/2013 | Grotz et al. | |
| 8,647,386 B2 | 2/2014 | Gordon | |
| 8,696,751 B2 | 4/2014 | Ashley et al. | |
| 8,771,360 B2 | 7/2014 | Jimenez et al. | |
| 8,894,710 B2 | 11/2014 | Simpson et al. | |
| 8,932,355 B2 | 1/2015 | Grotz et al. | |
| 8,940,049 B1 | 1/2015 | JImenez et al. | |
| 8,956,413 B2 | 2/2015 | Ashley et al. | |
| 8,992,620 B2 | 3/2015 | Ashley et al. | |
| 9,028,550 B2 | 5/2015 | Shulock et al. | |
| 9,358,125 B2 | 6/2016 | JImenez et al. | |
| 9,532,883 B2 | 1/2017 | McLuen et al. | |
| 9,622,878 B2 | 4/2017 | Grotz | |
| 11,013,617 B2 * | 5/2021 | Weiman | A61F 2/4611 |
| 11,191,650 B2 * | 12/2021 | Weiman | A61F 2/442 |
| 2002/0045945 A1 | 4/2002 | Liu | |
| 2002/0068976 A1 | 6/2002 | Jackson | |
| 2002/0068977 A1 | 6/2002 | Jackson | |
| 2002/0151978 A1 * | 10/2002 | Zacouto | A61F 2/3609 606/301 |
| 2003/0176926 A1 | 9/2003 | Boehm et al. | |
| 2004/0030387 A1 | 2/2004 | Landry et al. | |
| 2004/0049271 A1 | 3/2004 | Biedermann | |
| 2004/0054412 A1 | 3/2004 | Gerbec et al. | |
| 2004/0087947 A1 | 5/2004 | Lim et al. | |
| 2004/0153065 A1 | 8/2004 | Lim | |
| 2004/0210219 A1 * | 10/2004 | Bray | A61B 17/7059 606/279 |
| 2005/0021041 A1 | 1/2005 | Michelson | |
| 2005/0021145 A1 | 1/2005 | de Villiers et al. | |
| 2005/0033432 A1 | 2/2005 | Gordon | |
| 2005/0080422 A1 | 4/2005 | Otte et al. | |
| 2005/0113916 A1 | 5/2005 | Branch | |
| 2005/0143823 A1 * | 6/2005 | Boyd | A61B 17/8685 606/279 |
| 2005/0149188 A1 | 7/2005 | Cook | |
| 2005/0171541 A1 | 8/2005 | Boehm | |
| 2005/0209595 A1 * | 9/2005 | Karmon | A61M 31/002 606/76 |
| 2005/0228501 A1 * | 10/2005 | Miller | A61F 2/4425 606/264 |
| 2005/0251258 A1 | 11/2005 | Jackson | |
| 2005/0273171 A1 | 12/2005 | Gordon | |
| 2005/0273174 A1 | 12/2005 | Gordon | |
| 2005/0278026 A1 | 12/2005 | Gordon | |
| 2005/0283244 A1 | 12/2005 | Gordon | |
| 2005/0283245 A1 | 12/2005 | Gordon | |
| 2006/0004453 A1 | 1/2006 | Bartish, Jr. et al. | |
| 2006/0015184 A1 | 1/2006 | Winterbottom et al. | |
| 2006/0058790 A1 * | 3/2006 | Carl | A61B 17/70 606/248 |
| 2006/0058878 A1 | 3/2006 | Michelson | |
| 2006/0084986 A1 | 4/2006 | Grinberg et al. | |
| 2006/0122701 A1 | 6/2006 | Kister | |
| 2006/0129244 A1 | 6/2006 | Ensign | |
| 2006/0142859 A1 | 6/2006 | Mcluen | |
| 2006/0149385 A1 | 7/2006 | Mckay | |
| 2006/0195192 A1 | 8/2006 | Gordon et al. | |
| 2006/0229729 A1 | 10/2006 | Gordon | |
| 2006/0241770 A1 | 10/2006 | Rhoda et al. | |
| 2006/0253201 A1 | 11/2006 | Mcluen | |
| 2006/0265074 A1 * | 11/2006 | Krishna | A61B 17/7064 606/279 |
| 2007/0043442 A1 | 2/2007 | Abernathie | |
| 2007/0050030 A1 | 3/2007 | Kim | |
| 2007/0050032 A1 | 3/2007 | Gittings et al. | |
| 2007/0055377 A1 | 3/2007 | Hanson et al. | |
| 2007/0191951 A1 | 8/2007 | Branch | |
| 2007/0255415 A1 | 11/2007 | Edie et al. | |
| 2007/0270963 A1 | 11/2007 | Melkent et al. | |
| 2007/0270968 A1 | 11/2007 | Baynham | |
| 2008/0021559 A1 | 1/2008 | Thramann | |
| 2008/0065222 A1 | 3/2008 | Hamada | |
| 2008/0114467 A1 | 5/2008 | Capote et al. | |
| 2008/0140207 A1 | 6/2008 | Olmos et al. | |
| 2008/0147194 A1 | 6/2008 | Grotz et al. | |
| 2008/0161933 A1 | 7/2008 | Grotz et al. | |
| 2008/0167657 A1 | 7/2008 | Greenhalgh | |
| 2008/0183204 A1 | 7/2008 | Greenhalgh et al. | |
| 2008/0221694 A1 | 9/2008 | Warnick et al. | |
| 2008/0275455 A1 | 11/2008 | Berry et al. | |
| 2008/0281346 A1 | 11/2008 | Greenhalgh et al. | |
| 2008/0288073 A1 | 11/2008 | Renganath et al. | |
| 2008/0300598 A1 | 12/2008 | Barreiro et al. | |
| 2008/0306488 A1 | 12/2008 | Altarac et al. | |
| 2008/0319487 A1 | 12/2008 | Fielding et al. | |
| 2008/0319549 A1 | 12/2008 | Greenhalgh et al. | |
| 2009/0024217 A1 | 1/2009 | Levy et al. | |
| 2009/0062833 A1 | 3/2009 | Song | |
| 2009/0076616 A1 | 3/2009 | Duggal et al. | |
| 2009/0125062 A1 | 5/2009 | Amin | |
| 2009/0149956 A1 | 6/2009 | Greenhalgh et al. | |
| 2009/0149959 A1 | 6/2009 | Conner et al. | |
| 2009/0204218 A1 | 8/2009 | Richelsoph | |
| 2009/0222100 A1 | 9/2009 | Cipoletti et al. | |
| 2009/0240334 A1 | 9/2009 | Richelsoph | |
| 2009/0270989 A1 | 10/2009 | Conner et al. | |
| 2009/0281628 A1 | 11/2009 | Oglaza et al. | |
| 2009/0292361 A1 | 11/2009 | Lopez | |

(56) References Cited

U.S. PATENT DOCUMENTS

| | | |
|---|---|---|
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger et al. |
| 2010/0234894 A1* | 9/2010 | Alamin ............... A61B 17/7067 606/279 |
| 2010/0262239 A1* | 10/2010 | Boyden ............... A61F 2/30 600/587 |
| 2010/0286783 A1 | 11/2010 | Lechmann et al. |
| 2011/0035011 A1 | 2/2011 | Cain |
| 2011/0093074 A1 | 4/2011 | Glerum et al. |
| 2011/0160861 A1 | 6/2011 | Jimenez et al. |
| 2011/0172774 A1 | 7/2011 | Varela |
| 2011/0276142 A1 | 11/2011 | Niemiec et al. |
| 2011/0301713 A1 | 12/2011 | Theofilos |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0109308 A1 | 5/2012 | Echmann et al. |
| 2012/0130496 A1 | 5/2012 | Duffield et al. |
| 2012/0165945 A1 | 6/2012 | Hansell et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265309 A1* | 10/2012 | Glerum ............... A61F 2/447 623/17.16 |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | McLaughlin et al. |
| 2013/0023993 A1* | 1/2013 | Weiman ............... A61F 2/4611 623/17.16 |
| 2013/0023994 A1 | 1/2013 | Glerum |
| 2013/0073045 A1* | 3/2013 | Vestgaarden ............ A61F 2/447 623/17.16 |
| 2013/0158663 A1 | 6/2013 | Miller et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2014/0067071 A1 | 3/2014 | Weiman et al. |
| 2014/0088714 A1 | 3/2014 | Miller et al. |
| 2014/0163683 A1 | 6/2014 | Seifert et al. |
| 2015/0005880 A1* | 1/2015 | Popa ............... A61F 2/446 623/17.13 |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0030194 A1* | 2/2016 | Ledet ............... A61F 2/44 623/17.16 |
| 2016/0166396 A1* | 6/2016 | McClintock ............ A61F 2/446 623/17.16 |
| 2016/0324654 A1 | 11/2016 | Loebl et al. |
| 2017/0020683 A1* | 1/2017 | Bray, Jr. ............... A61F 2/4465 |
| 2017/0100258 A1 | 4/2017 | Jimenez et al. |
| 2017/0119543 A1* | 5/2017 | Dietzel ............... A61F 2/28 |
| 2017/0333204 A1* | 11/2017 | Huang ............... A61F 2/447 |
| 2020/0375634 A1* | 12/2020 | Field ............... A61F 2/4405 |
| 2023/0136813 A1* | 5/2023 | Cordonnier ............ G16H 20/40 705/2 |

FOREIGN PATENT DOCUMENTS

| | | |
|---|---|---|
| DE | 4012622 C1 | 7/1991 |
| DE | 4327054 C1 | 4/1995 |
| EP | 0576379 B1 | 6/1993 |
| EP | 0610837 B1 | 7/1994 |
| EP | 3111896 A1 | 1/2017 |
| FR | 2794968 A1 | 12/2000 |
| JP | 2000-513263 A | 10/2000 |
| KR | 200290058 Y1 | 9/2002 |
| SU | 1424826 A1 | 9/1988 |
| WO | 9201428 A1 | 2/1992 |
| WO | 9525485 A1 | 9/1995 |
| WO | 1999042062 A1 | 8/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2010103344 A1 | 9/2010 |
| WO | 2012031267 A1 | 3/2012 |
| WO | 2015009793 A1 | 1/2015 |

* cited by examiner

REVERSE DYNAMIZATION IMPLANTS

FIELD OF THE INVENTION

The present disclosure generally relates to devices and methods for orthopedics, and more particularly relates to implants that facilitate the bone fusion process.

BACKGROUND OF THE INVENTION

In orthopedics, one or more bones that are damaged, diseased, or degenerated may be fixed together to promote bone healing. The bone fixation may occur, for example, between vertebrae in the spine, to stabilize fractures in long bones, or other suitable treatment of bone(s) or bone fragments. Degeneration and deformity of the spine may be treated with interbody spacers, which aid in indirect decompression of neural elements. In cases where significant disc height restoration is needed or endplate disruption should be minimized, the use of an expandable interbody may be advantageous. This allows the user to insert the cage with a given, shorter starting height and expand the cage to reach final height, yielding greater disc height restoration than may be possible with a static cage. The current standard of care for fractures of long bones (bones that are longer than they are wide) may involve either open reduction with internal fixation (ORIF) or closed reduction with intramedullary fixation, based on the severity of injury (fracture displacement, comminution, soft tissue involvement, etc.) and the anatomy involved.

Historically, the standard of care for bone fixation has focused on dynamization where the bones are first rigidly fixed with total bone immobilization and over time, an increase in movement may be introduced to help promote bone growth and healing. The process of bone healing, however, may be influenced by a number of complicated factors related to biology and biomechanics. There exists a need for fixation devices that minimize the occurrence of delayed union and nonunion, promote new bone growth, and/or reduce the overall healing time of bone.

SUMMARY OF THE INVENTION

To meet this and other needs, devices, systems, and methods for bone fixation are provided. In particular, implants configured to promote reverse dynamization are provided. With reverse dynamization, rather than rigidly fixating two bone pieces following fracture reduction, a semi-rigid implant secures the fracture site, which permits micro-motion for a set period of time, followed by rigid fixation. This initial period of dynamization, prior to final fixation, may create an increase in callous tissue volume, faster fusion, and/or increased resistance to torsion failure. The reverse dynamization process may enhance the speed at which callus ossification occurs, thereby leading to earlier healing of the fracture. The principals of reverse dynamization may be applied throughout the body in order to accelerate bone healing more consistently, especially in weight bearing conditions, and obtain superior bone fracture healing, thereby minimizing the occurrence of delayed union or nonunion.

According to one embodiment, a system for reverse dynamization includes an implant configured to be secured to bone. The implant has one or more moveable components creating a semi-rigid configuration to allow for micro-motion of the bone for a period of time. The moveable component(s) are changeable to a static condition creating a rigid configuration to prevent subsequent movement of the bone. The implant may be an expandable spinal implant, a bone plate, or an intramedullary nail, for example. The moveable component(s) may be locked post-operatively. The moveable component(s) may be changed to the static condition by manipulation or activation. The moveable component(s) may be changed to the static condition by a material property change. Micro-motion of the bone may be permitted for the first 2-6 weeks of healing, for example.

According to another embodiment, an expandable implant includes a front ramp having at least one ramped surface and a rear ramp having at least one ramped surface, a central drive screw retained in the rear ramp and threadedly engaged with the front ramp, an upper endplate and a lower endplate, each slidably engaged with the ramped surfaces of the front and rear ramps, respectively, wherein rotation of the central drive screw moves the front ramp toward the rear ramp forcing the upper and lower endplates outward, thereby expanding a height of the implant, and a reverse dynamization component located along the central drive screw, the reverse dynamization component being flexible to provide for micro-motion for a given period of time, and subsequently, stiffens to rigidly fix the upper and lower endplates.

The expandable implant may have one or more of the following attributes. The reverse dynamization component may be a washer. While flexible, the reverse dynamization component may have an axial width that is variable in nature for the given period of time. The reverse dynamization component may be housed along a long axis of the central drive screw such that the axial width contributes to a total distance between the front and rear ramps. A height across the upper and lower endplates may change in proportion to a change in the axial width of the reverse dynamization component. The reverse dynamization component may be formed of a cross-linking polymer that cross-links to due to repeated strain. The reverse dynamization component may be formed of a two-part curing material with each part housed in separate compartments separated by a barrier, and when the barrier breaks and the two-parts mix, the resulting mixture cures and stiffens. The reverse dynamization component may be a work-hardened spring that stiffens as the spring is overloaded and repeatedly deformed.

According to another embodiment, a construct includes a bone plate with a plurality of through openings configured to be secured to bone, a plurality of bone fasteners having a head and a threaded shaft positioned through each of the respective through openings in the bone plate, and a reverse dynamization component configured to allow for micro-motion of the bone for a period of time and then form a rigid configuration to prevent subsequent movement of the bone.

The construct may have one or more of the following attributes. The reverse dynamization component may be a locking member positioned adjacent to the head of the bone fastener, wherein the locking member has a first state to allow for the micro-motion and a second state to allow for rigid locking of the bone fasteners. The reverse dynamization component may be formed of a shape-memory material that is activated due to an external stimulation to change from the first state to the second state. The reverse dynamization component may be a strip attached along a longitudinal length of each edge of the bone plate, wherein the strip is configured to change stiffness due to an activation. The reverse dynamization component may be a strip attached along a longitudinal length of each edge of the bone plate, wherein the strip is configured to change stiffness as the strip absorbs fluid over time. The plate itself may be configured to absorb fluid and change stiffness over time. The reverse dynamization component may be a patch implantable along a bottom of the bone plate or along the bone fasteners, wherein the patch includes time release nutrients.

According to another embodiment, an intramedullary nail includes two movable components that provide micromotion along a longitudinal axis of the nail. The two moveable components include a distal tip and a proximal body. The distal tip has an extension receivable in a central opening through the proximal body. A dynamic member is positioned between the two moveable components to allow controlled movement between the moveable components. A mechanical lock is configured to stop motion between the moveable components.

The intramedullary nail may have one or more of the following attributes. The dynamic member may be a spring, Belville washer, or polymer spacer/washer. The mechanical lock may include a central locking rod extending through the proximal body and into the extension of the distal tip. The locking rod may include a locking member at its free end configured to interface with the inside of the distal tip. The locking member may be a ratcheting lock, a caulk gun clamp, or a one way clutch. The nail may have an internal antenna such that the nail may be locked post operatively with wireless communication.

According to yet another embodiment, a method to promote bone healing may include, in any suitable order: (1) affixing an implant to bone; (2) permitting micro-motion of the bone for a period of time, for example, about 2-6 weeks; (3) altering a reverse dynamization component of the implant to create a rigid result. For example, the implant may be adjusted mechanically, electronically, through a material property change, by mixing curable components, or by adding additional ingredients that harden over time. The changes may occur post-operatively without the need for further surgical intervention. In one example, a reverse dynamization component may be altered externally, for example, by a stimulation, such as ultrasound, electromagnetic, radio frequency, thermal, etc.

According to yet another embodiment, a kit may include a plurality of implants of different sizes and configurations. The kit may further include one or more devices suitable for installing and/or removing the assemblies described herein, such as insertion devices or drivers; one or more removal devices; and other tools and devices, which may be suitable for surgery.

BRIEF DESCRIPTION OF THE DRAWINGS

The present embodiments will become more fully understood from the detailed description and the accompanying drawings, wherein.

DETAILED DESCRIPTION

Figure 1A:
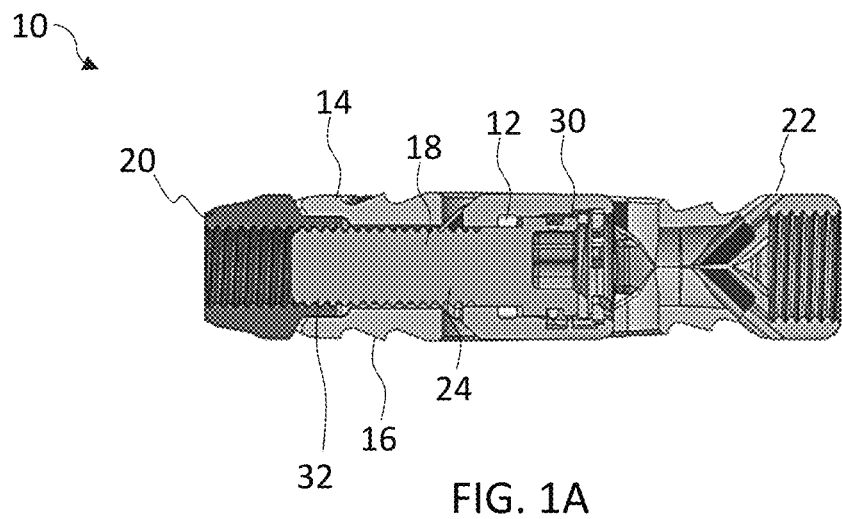
FIGS. 1A-1B illustrate cross-sectional views of an expandable spinal implant in collapsed and expanded configurations, respectively, with a reverse dynamization component for permitting micromotion of the implant for a period of time according to one embodiment.

Embodiments of the disclosure are generally directed to devices, systems, and methods for reverse dynamization bone fixation. Specifically, the implants described herein apply the principals of reverse dynamization by allowing for micromotion of a fracture to build callus rapidly and then for subsequent rigidity of the implant allowing the callus to form bone. The implant may first create a semi-rigid fracture fixation construct, accelerating the formation of callus, and after a set period of time, the fixation construct may change or be modified to be mostly or completely rigid. The reverse dynamization process may enhance the speed at which callus ossification occurs and lead to earlier healing of the fracture.

The implants may include spinal implants, bone plates, intramedullary nails, or other bone fixation devices. In spinal applications, the implants may be configured to be implanted in the intervertebral disc space situated between two adjacent vertebrae. The implant may be an expandable implant with one or more internal reverse dynamization components configured to initially impart micromotion to the device and subsequently change form, state, or size to rigidly secure the implant. For example, the expandable interbody implant may allow the process of reverse dynamization to be induced in the disc space through the natural movement of the post-operative patient, which may yield faster and stronger interbody fusion outcomes.

The implants may be implanted through an open, semi-open, or minimally invasive surgery (MIS). Minimally invasive surgery may be used to preserve muscular anatomy, reduce post-operative pain, and improve recovery time for patients. It will be readily appreciated by those skilled in the art that the implant may be employed in any number of suitable orthopedic approaches and procedures, including but not limited to, anterior, posterior, lateral, anterolateral, or posterolateral approaches to the lumbar spine, cervical spine, or thoracic spine.

In long bone applications, the implant may include one or more bone plates positionable along the long bone to brace the fracture(s). The plates may be adapted to contact one or more of a femur, a tibia, a humerus, a clavicle, a fibula, an ulna, a radius, bones of the foot, bones of the hand, or other suitable bone(s) or fragments thereof. The bone plate may be secured with one or more bone fasteners, such as bone screws. The bone plate may include one or more dynamization components configured to lock the bone screws, increase the rigidity of the bone plate itself, and/or supplement the bone plate or overall construct.

In other applications, the long bones may be secured with an intramedullary nail configured to be positioned inside the intramedullary canal. The intramedullary nails may be adapted for a femur, tibia, a humerus, or other long bone. The intramedullary nail may provide for reverse dynamization by being initially moveable and subsequently fixed to treat the fractures of long bones. Although expandable implants, bone plates, and intramedullary nails are exemplified herein, it will be appreciated that the principals of reverse dynamization described herein may be applied to other areas of the body to enhance or accelerate bone healing, minimize the likelihood of delayed union or non-union, and/or achieve superior surgical results.

Figure 1B:
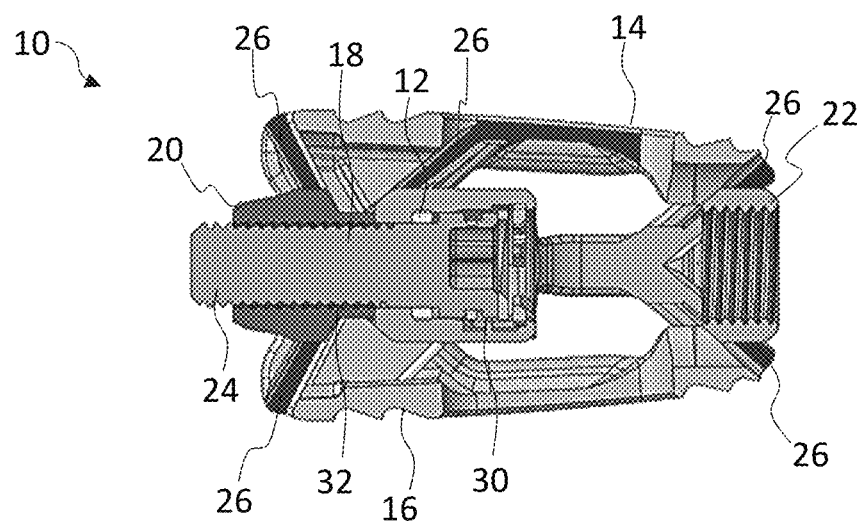
Figure 2:
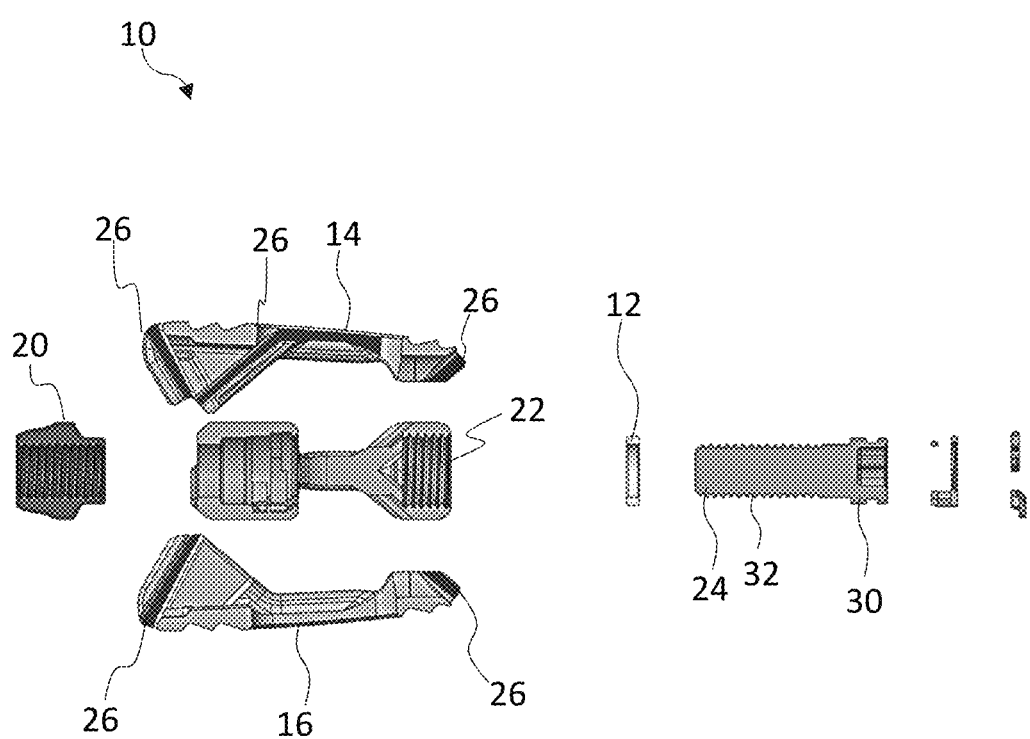
FIG. 2 shows an exploded view of the expandable implant of FIGS. 1A-1B.

Turning now to the drawing, where like reference numerals refer to like elements, FIGS. 1A-1B illustrate an expandable implant 10 with a reverse dynamization component 12 configured to impart micromotion to the implant 10. A spinal fusion is typically employed to eliminate pain caused by the motion of degenerated disc material. Upon successful fusion, the fusion device 10 becomes permanently fixed within the intervertebral disc space. As shown in FIG. 1A, the expandable fusion device 10 may be positioned between adjacent vertebral bodies in a collapsed position. As shown in FIG. 1B, the expandable fusion device 10 is configured to expand in height such that the implant 10 engages the endplates of the adjacent vertebral bodies. FIG. 2 depicts an exploded view of the device 10.

The expandable implant 10 is configured to incorporate reverse dynamization in order to obtain superior bone fracture healing. Rather than rigidly fixating two bone pieces immediately, the site is allowed micromotion for a set period of time. Micromotion may be permitted for the first few days, weeks, or months of healing. For example, micromotion may be permitted for the first 1-10 weeks, 1-8 weeks, 2-8 weeks, or 2-6 weeks of healing. Subsequently, after the initial time period, the implant 10 provides for rigid fixation. This early period of dynamization may create an increase in callous tissue volume, faster fusion, and increased resistance to torsion failure. A compliant, expandable interbody spacer 10 that allows the process of reverse dynamization to be induced in the disc space through the natural movement of the post-operative patient may yield faster and stronger interbody fusion outcomes.

The expandable fusion device 10 extends along a central longitudinal axis between front and rear ends of the device 10. The expandable implant 10 includes a top or upper endplate 14 and a bottom or lower endplate 16. The upper and lower endplates 14, 16 may be the same or mirror images of one another. The upper and lower endplates 14, 16 are configured to engage with the endplates of the adjacent vertebral bodies and, in the expanded position, the expanded device 10 is configured to maintain intervertebral disc spacing and restore spinal stability, thereby facilitating the intervertebral fusion. One or more of the endplates 14, 16 may include a plurality of teeth, protrusions, or other friction enhancing surfaces configured to engage bone. The endplates 14, 16 may include one or more graft openings or windows configured to receive bone graft or other suitable bone growth enhancing material.

It should be understood that references to the front and rear ends and upper and lower endplates 14, 16 are described with respect to the direction of placement into an intervertebral disc space with the front of the expandable fusion device 10 placed into the disc space first, followed by the rear of the expandable fusion device 10. These and other directional terms may be used herein for descriptive purposes and do not limit the orientation(s) in which the devices may be used.

The upper and lower endplates 14, 16 are configured to be expanded by an actuation assembly 18. The actuation assembly 18 may include a front ramp 20, a rear ramp 22, and a central drive screw 24. One or both of the ramps 20, 22 may be moveable via rotation of the central drive screw 24. In one embodiment, the front ramp 20 is a moveable dynamic ramp and the rear ramp 22 is a stationary static ramp 22. It will be appreciated that the actuation assembly 18 may include additional ramps, the static and dynamic ramps may be reversed, or both ramps may be moveable.

In this embodiment, the actuation assembly 18 causes outward movement of the upper and lower endplates 14, 16 relative to one another. The central drive screw 24 includes a head portion 30 secured in the rear ramp 22 and a threaded portion 32 threadedly engaged with a corresponding threaded bore through the front ramp 20. The inner facing surfaces of the upper and lower endplates 14, 16 may include one or more ramped surfaces 26 configured to engage with corresponding ramped surfaces on the front and rear ramps 20, 22, respectively. In particular, the top and bottom endplates 14, 16 have ramped surfaces 26 which interact with the dynamic front ramp 20, and the dynamic front ramp 20 may be driven by rotation of the central drive screw 24. The central drive screw 24 may be housed in the stationary rear ramp 22, which also has ramped surfaces engaged with the corresponding endplate ramps 26. As the drive screw 24 is driven, the distance between the dynamic and stationary ramps 20, 22 is shortened, and the ramped interfaces force the endplates 14, 16 to expand in a direction orthogonal to the long axis of the driving screw 24.

Expandable implants are described in more detail in U.S. Pat. Nos. 11,344,430; 11,191,650; and 11,013,617, which are incorporated by reference herein in their entireties for all purposes. Although the ramp/screw combination is exemplified, it will be appreciated that any suitable mechanism capable of achieving the function of expansion for the expandable interbody spacer 10 may be used.

While the central drive screw 24 actuates to change the distance between the dynamic and stationary ramps 20, 22, there are other components whose width or thickness in the axial direction contribute to that distance. For example, one or more thrust bearings 12, such as PEEK washers, may be used as a smooth bearing surface and as a measure to prevent unintentional drift of the drive screw 24. In one embodiment, one or more of these additional components, such as thrust bearing 12, act as a reverse dynamization component to dynamically change in width after the user has driven the screw 24 to the desired position. In this manner, the height across the endplates 14, 16 are configured to change in proportion to the change in component width or thickness. Similarly, other reverse dynamization components 12 may be substituted or added to influence the actuation mechanism and provide for micromotion of the device 10.

The reverse dynamization component 12 may have an axial width that is variable in nature for a period of time. The reverse dynamization component 12 may be housed along the long axis of the main screw 24 such that the axial width contributes to the total distance between the dynamic and stationary ramps 20, 22. For example, the reverse dynamization component 12 may have a property that changes its stiffness over time. Initially, the reverse dynamization component 12 may be more pliable, springy, or elastic. Over time, however, the component 12 becomes more stiff, rigid, or inelastic. Thus, the early compliance of the reverse dynamization component 12 allows for the distance between the dynamic and static ramps 20, 22, and therefore, height across endplates 14, 16, to change as the implant 10 is cyclically loaded by the patient's movement. As the stiffness increases, the allowed change in axial distance and height across endplates decreases, rigidly fixing the implant 10 and achieving the reverse dynamization outcome.

Accordingly, in one embodiment, the reverse dynamization component 12 may have a variable width, a flexibility, a change in state, or other alteration in type or parameter that permits for initial movement, thereby resulting in micromotion. Subsequently, after a given period of time or a certain change in conditions, the reverse dynamization component 12 may have a more rigid or stiff configuration, thereby forming the final rigid construct. For example, the reverse dynamization component 12 may have a material property or mechanical design that changes its stiffness over time.

In one embodiment, the reverse dynamization component 12 is a compliant component made from a cross-linking polymer. In polymers, cross-linking is the process by which long polymer chains connect to one another, increasing the overall stiffness of the material. In some polymers, increased cross-linking may be induced by repeated strain, thus making the material stiffer as it is cyclically deformed. The reverse dynamization component 12 undergoes cyclical loading due to movement of the patient, thereby resulting in an increase in stiffness when the component 12 is comprised of a cross-linking polymeric material.

In another embodiment, the reverse dynamization component 12 includes a two-part, slow curing material. Two-part curing materials may be used in biocompatible applications, such as bone cement. One component contains the structural building blocks and the other component acts as a catalyst that constructs the building blocks when the two parts are mixed together. Cure rate and final material properties may be manipulated by controlling the ratio of the two components. The reverse dynamization component 12 may be comprised of two compartments with a barrier separating them. When the barrier is broken, the slow-curing process begins yielding the slow stiffness increase desired.

Figure 3:
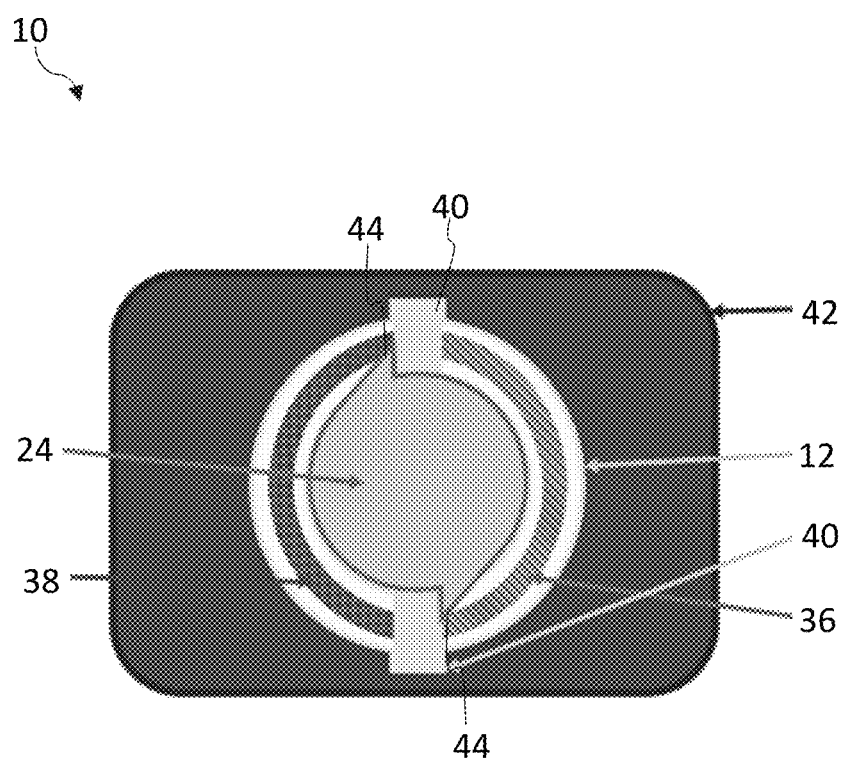
FIG. 3 depicts the expandable implant having a two-part curing assembly according to one embodiment.

FIG. 3 depicts one example of the reverse dynamization component 12 including two separate compartments 36, 38 with a barrier or divider 40 in between, which is configured to rupture to allow the curing materials to mix together. In one embodiment, actuation of the drive screw 24 causes mixing of the two material components. The first compartment 36 may hold a first material and the second compartment 38 may hold a second material of the two-part system. The reverse dynamization component 12 may be located in a housing 42 or may be otherwise positioned between the upper and lower endplates 14, 16. The reverse dynamization component 12 may be positioned along the length of the central drive screw 24. For example, the drive screw 24 may include one or more cams 44 configured to break the compartment divider(s) 40 when actuated. In the embodiment shown, the compartments 36, 38 are separated by two dividers 40, which are broken by two respective cams 44, although it will be appreciated that any suitable type and number of dividers 40 and cams 44 may be used to complete the process. The barrier or divider(s) 40 may be broken when the screw 24 is rotated, for example, and the slow-curing process begins yielding the slow stiffness increase desired.

In yet another embodiment, the reverse dynamization component 12 includes a work-hardened spring. Conventional helical springs and short-throw wave springs are usually used in applications where their load does not exceed the yield load, preventing permanent deformation of the material. Work-hardening occurs when a material is intentionally plastically deformed, disrupting the usually regular crystalline structure of the material, and increasing resistance to further structure disruption, resulting in a stiffer material. A conventional spring, sized correctly and intentionally overloaded may increase its spring resistance over time, achieving the reverse dynamization outcome. The work-hardened spring may be composed of metal, polymer, or another material.

It may be advantageous to choose stiffness values and arrangements of components such that the reverse dynamization component 12 is compressed to its full state when loadbearing and as load is lightened (such as at the highest point in a walking stride or at the peak of a jump), the reverse dynamization component 12 expands. This maintains implant endplate contact with vertebral endplates regardless of loading and mitigates risk of migration, while still allowing the movement required for reverse dynamization. The process of reverse dynamization may result in superior healed bone volume and increased resistance to torsional failure of the healed bone. The expandable interbody spacer 10 allows for reverse dynamization to occur across the disc space and may lead to faster and stronger fusion outcomes.

Turning now to FIGS. 4-8, the implant 60 is a bone plate configured to be secured to bone with a plurality of bone fasteners 62. In each embodiment, the bone plate 60 includes one or more reverse dynamization components configured to increase the strength and/or rigidity of the construct over time. Using reverse dynamization, initially the implant 60 acts as a semi-rigid fracture fixation construct, accelerating the formation of callus, and after a set period of time, the fixation construct changes or is modified to be completely rigid. The bone fracture fixation construct may be modified to increase stiffness and increase construct rigidity postoperatively and achieve accelerated healing via reverse dynamization. This process may enhance the speed at which callus ossification occurs and lead to earlier healing of the fracture.

The bone plates 60 described herein may be adapted to contact one or more of a femur, a distal tibia, a proximal tibia, a proximal humerus, a distal humerus, a clavicle, a fibula, an ulna, a radius, bones of the foot, bones of the hand, or other suitable bone or bones. The bone plates may be curved, contoured, straight, or flat. Optionally, the plates may have a head portion that is contoured to match a particular bone surface, such as a condylar region, metaphysis or diaphysis. In addition, the plates may have a shaft portion that is contoured to match a particular surface that flares out in the form of an L-shape, T-shape, Y-shape, etc. The plates may be adapted to secure small or large bone fragments, single or multiple bone fragments, or otherwise secure one or more fractures. In particular, the systems may include a series of trauma plates and screws designed for the fixation of fractures and fragments in diaphyseal and metaphyseal bone. Different bone plates may be used to treat various types and locations of fractures.

Figure 4A:
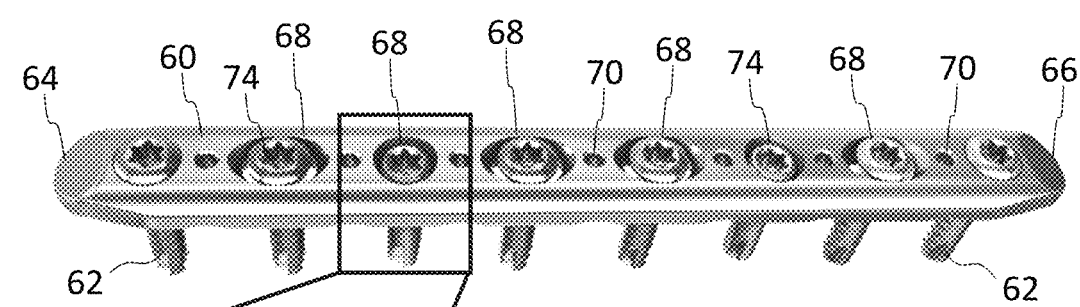
FIGS. 4A-4C shows a bone plate implant with reverse dynamization components configured to secure the heads of the bone screws according to one embodiment.

In the embodiment shown in FIG. 4A, the bone plate 60 is a straight plate that extends from a first end 64 to a second end 66 along a longitudinal axis. One or both of the ends 64, 66 may be tapered, for example, to facilitate insertion and/or placement. The bone plate 60 defines a series of holes or openings 68 configured to receive one or more bone screws or fasteners 62. The openings 68 may be locking holes, non-locking holes, or otherwise configured to receive the bone fastener 62. The bone fasteners 62 may include polyaxial or fixed angle fasteners, for example. The plate 60 may also define one or more k-wire holes 70 configured for receiving a k-wire therein to guide the bone plate 60 to a desired surgical site. Suitable bone plates, openings, and fasteners are described in more detail in U.S. Pat. Nos.

11,197,701; 10,856,920; and 10,751,098, which are incorporated by reference herein in their entireties for all purposes.

Figure 4B:
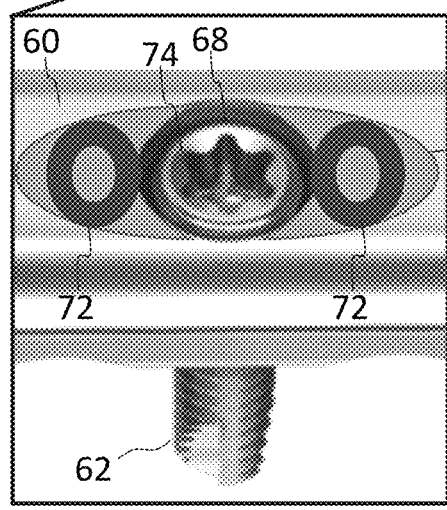
Figure 4C:
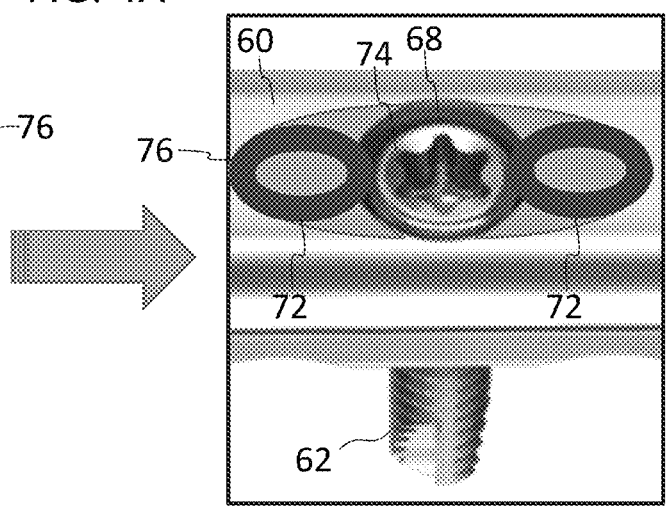

With further emphasis on FIGS. 4B-4C, the bone fasteners 62 may be secured to the bone plate 60 with one or more retaining or locking members 72 configured to change state over time or due to an external stimulation, for example. As shown in FIG. 4B, one or more locking members 72 may be positioned adjacent to a head 74 of the bone fastener 62 in a first state, position, or shape. For example, a pair of locking members 72 may be positioned on opposite sides of the screw head 74 and the locking members 72 may be generally circular in shape. The locking members 72 may be located in a recess 76 around each opening 68 through the plate 60. As shown in FIG. 4C, after a period of time or a stimulation, the locking members 72 transition to a different state, position, or shape. For example, the pair of locking members 72 may change to generally oval shape such that a portion of each locking member 72 engages or covers the top of the screw head 74, thereby rigidly securing the bone fastener 62 in the construct. Although circle and oval shapes are exemplified for the unlocked and locked shapes, respectively, it will be appreciated that other suitable shapes or configuration may be used to secure the bone fasteners 62 to the bone plate 60.

According to one embodiment, the locking members 72 are composed of a shape-memory material, such as nitinol. The nitinol mechanisms 72 may be installed onto or into the plate 60 during the manufacturing process. At the time of surgery, the screws 62 are installed through the plate 60 to stabilize the fracture per standard surgical techniques, but do not lock into the plate 60, producing a semi-rigid construct. After the initial healing period has passed and callus formation has occurred, the nitinol members 72 are configured to be activated and changed into a locked state. For example, the patient may undergo external stimulation, such as ultrasound, electromagnetic, radio frequency, thermal, etc. to activate the nitinol mechanism 72. When activated, the nitinol 72 changes shape and engages the heads 74 of the screws 62, thereby stiffening the construct and promoting accelerated callus ossification per reverse dynamization.

Figure 5:
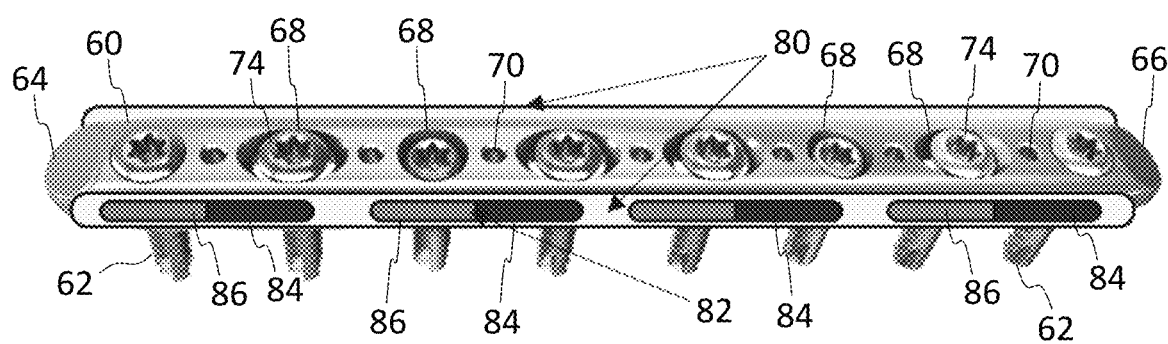
FIG. 5 shows a bone plate implant with breakable two-part assembly according to one embodiment.

Turning now to the embodiment shown in FIG. 5, the bone plate 60 may include one or more strips 80 with reverse dynamization sections 82 configured to harden over time or due to a given activation. In this embodiment, the implant 60 may include a ductile locking fracture fixation plate made from a metallic, polymer, or composite material. One or more strips 80 may be attached to or embedded within the plate 60, for example, along the longitudinal length of each edge of the implant 60. Positioned along the strips 80 or embedded therein one or more implantable sections 82 may be configured to change stiffness following activation. In one embodiment, the sections 82 may include first and second compartments 84, 86 containing two separate components that harden when mixed. For example, breakable sections 82 may include cylinders containing, in an isolated and unmixed state within each respective cylinder, the required component materials to form bone cement, two-part epoxy, or other similar multicomponent material such that when mixed, a hardened composite structure is formed. Although cylinders 82 are exemplified, it will be appreciated that any suitable structure may be selected to contain the respective components and thereafter permit mixing at an appropriate time.

At the time of surgery, locking screws 62 are installed into the ductile locking plate 60 to stabilize the fracture per standard surgical techniques, producing a semi-rigid construct due to the inherent ductility of the substrate material. After the initial healing period has passed, and callus formation has occurred, the patient may undergo external stimulation to cause the isolated materials in each respective cylinder 82 to combine and mix together, activating a chemical reaction within each cylinder 82. The external stimulation may include ultrasound, electromagnetic, radio frequency, thermal, mechanical, or other suitable activation of the components. After being activated and mixed together, the composite material subsequently hardens, thereby creating an overall stiffer construct, and promoting accelerated callus ossification.

Figure 6:
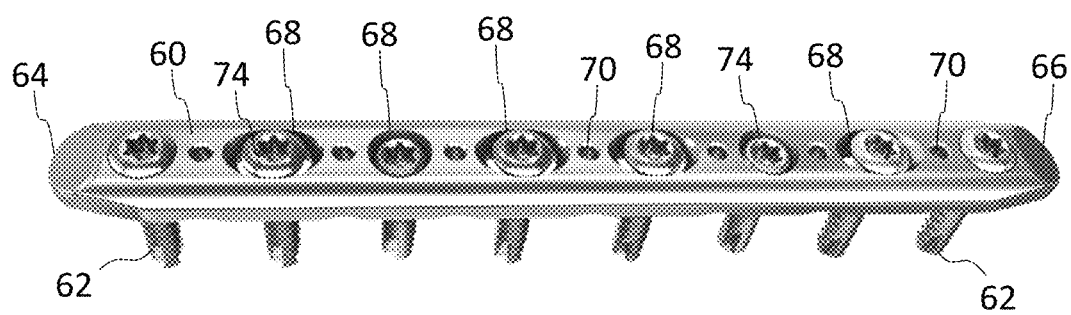
FIG. 6 shows an example of a bone plate implant configured to change state over time according to one embodiment.

Turning now to the embodiment shown in FIG. 6, the bone plate 60 itself may be configured to change stiffness over time or due to an activation event. For example, the plate 60 may be composed of a material configured to absorb fluid over time, which gradually becomes stiffer. In this embodiment, the plate 60 is made from a material that exhibits unique fluid absorption properties such that when fluid is absorbed, the material gradually becomes stiffer. The rate of fluid absorption of the material is tuned to correlate with the rate of fracture healing, so that by the time abundant callus formation has occurred, the implant 60 has become stiff enough to promote enhanced callus ossification and fracture healing. At the time of surgery, metallic screws 42 are installed into the plate 60 to stabilize the fracture per standard surgical techniques, producing a semi-rigid construct due to the inherent ductility of the substrate material. Immediately following implantation, the construct gradually becomes stiffer as fluid is absorbed into the plate 60, thereby promoting accelerated fracture healing.

Figure 7:
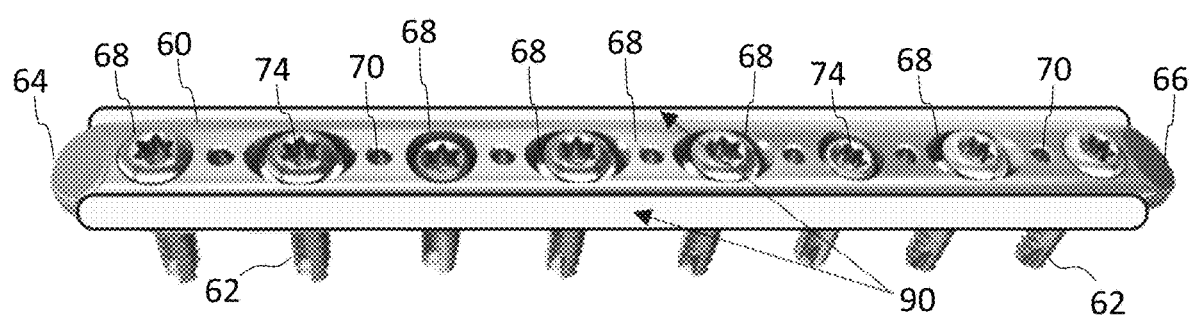
FIG. 7 shows reverse dynamization strips along the edges of the bone plate implant according to one embodiment.

Turning now to the embodiment shown in FIG. 7, the bone plate 60 may include one or more strips 90 configured to harden over time or due to a given activation. In this embodiment, the implant 60 may include a ductile locking fracture fixation plate made from a metallic, polymer, or composite material. Attached to the plate 60, along the longitudinal length of the implant 60, are either a single or plurality of strips 90. Alternatively, the strips 90 may be embedded in the plate 60 or otherwise located along its body. The strips 90 may be made from a material that exhibits unique fluid absorption properties such that when fluid is absorbed, the material gradually becomes stiffer. The rate of fluid absorption of the material is tuned to correlate with the rate of fracture healing, so that by the time abundant callus formation has occurred, the implant 60 has become stiff enough to promote enhanced callus ossification and fracture healing.

At the time of surgery, metallic screws 62 are installed into the plate 60 to stabilize the fracture per standard surgical techniques, producing a semi-rigid construct due to the inherent ductility of the substrate material. Immediately following implantation, the strips 90 begin absorbing fluid resulting in the construct gradually becomes stiffer. The amount and rate of absorption is tuned to achieve maximum stiffness by the time that adequate callus formation is achieved, enhancing the speed at which fracture healing occurs.

Figure 8:
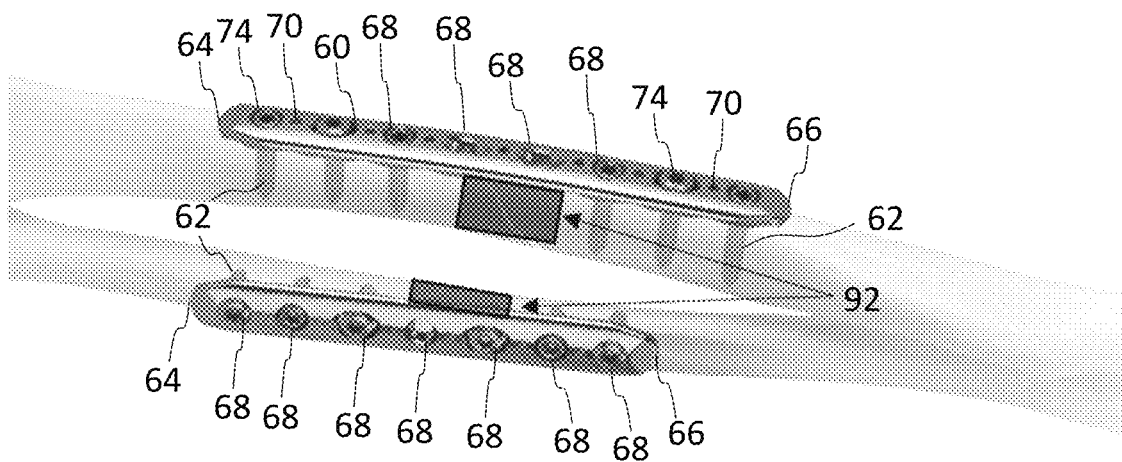
FIG. 8 shows two bone plate implants affixed to the radius and ulna with implantable time release strips according to one embodiment.

Turning now to the embodiment shown in FIG. 8, the bone plate(s) 60 may be supplemented with one or more reverse dynamization patches 92. The patch 92 may be implanted alongside, near, or in contact with the construct to increase stiffness over time. For example, a patch 92 may be positioned adjacent to or in contact with the bottom of the plate 60 and/or along the bone fasteners 62 to increase rigidity over time. As shown, one plate 60 may be affixed to a first bone, such as the ulna, and a second plate 60 may be affixed to a second bone, such as the radius, and a plurality of strips or patches 92 may be added across the fracture sites. It will be appreciated that the patch 92 may be of any suitable size and shape and positioned at any suitable location by the surgeon.

The patch 92 may be a strip, area, or section, which acts as a bioresorbable nutrient matrix. In one embodiment, the patch 92 may be a time release strip configured to be applied to the fracture at the time of surgical repair. The patch 92 may include a mix of nutrients and compounds that facilitate the biologic calcification of callus. The properties of the patch 92 are tuned such that the release of the nutrients and compounds is initiated after a period of time that coincides with the time at which adequate callus formation has been achieved. The resulting nutrient and compound emission delivers the nutrition needed directly to the fracture site to enhance the speed and quality of fracture healing.

Figure 9:
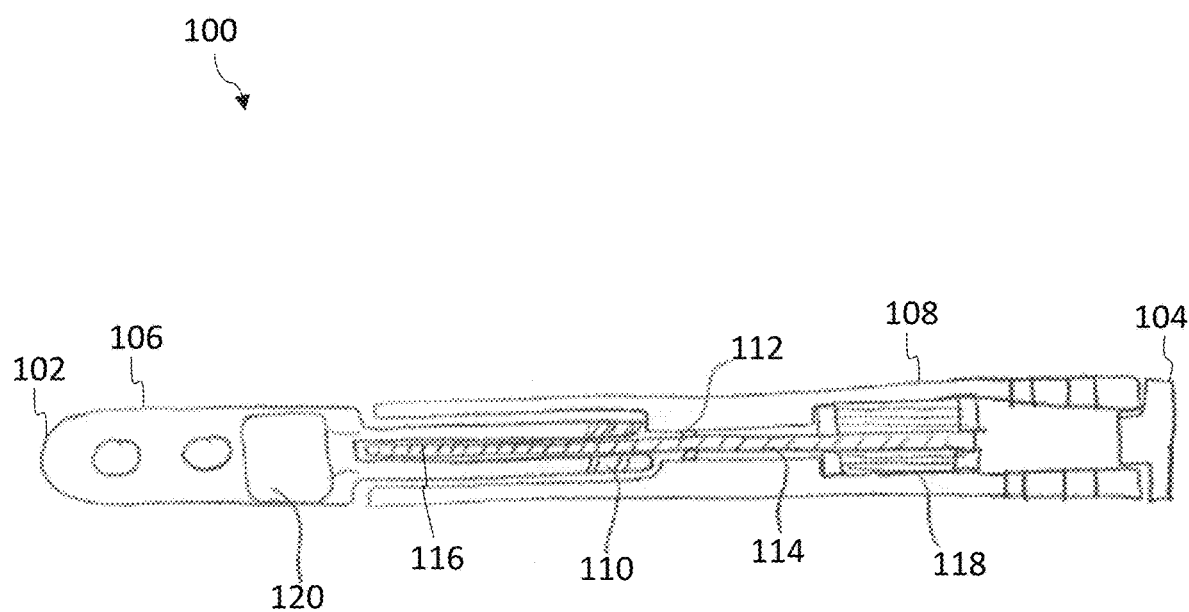
FIG. 9 shows a moveable intramedullary nail according to one embodiment.

Turning now to FIGS. 9-11, the implant 100 is an intramedullary nail that applies the principals of reverse dynamization by first allowing micro-motion at the fracture to build callus rapidly and then post-operatively locking the implant rigidly, thereby allowing the callus to form bone. Reverse dynamization may be applied throughout the body to accelerate bone healing more consistently, especially in weight bearing conditions. Non-invasive post operative manipulation or activation of the implant 100 may be used to lock or turn-off the dynamization/motion of the implant allowed at time of implantation.

As best seen in FIG. 9, the intramedullary nail 100 may comprise a generally elongate body extending from a first, distal portion or end 102 to a second, proximal portion or end 104. The elongate body may be in the form of an elongate tubular rod configured to extend longitudinally within the intramedullary canal of a fractured bone. The elongate body may be substantially straight along a longitudinal axis of the nail 100 or may comprise one or more curves or bends to conform to the anatomical shape of the intramedullary canal of the bone (e.g., femur, tibia). Intramedullary nail implants are described in more detail in U.S. Pat. No. 11,213,337, which is incorporated by reference herein in its entirety for all purposes.

Figure 10A:
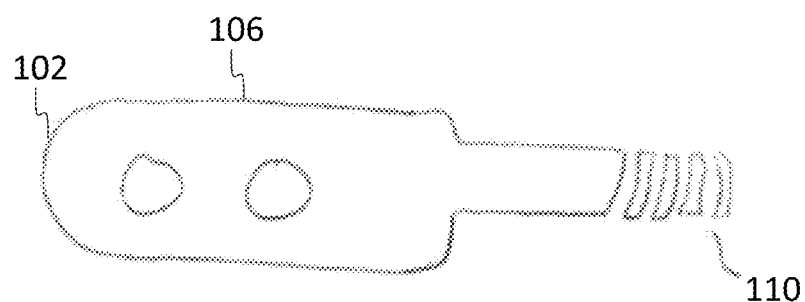
FIGS. 10A-10C illustrate alternative examples of the dynamic member of the intramedullary nail.
Figure 10B:
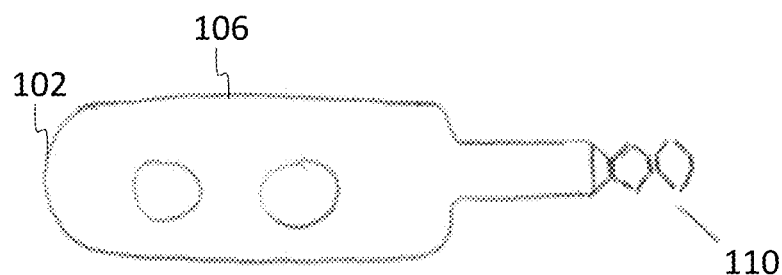
Figure 10C:
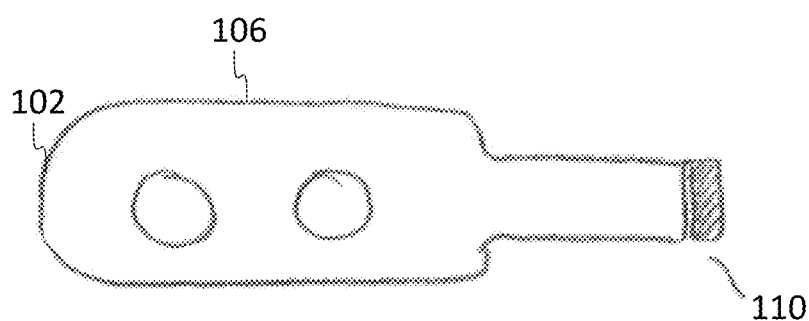

In this embodiment, the intramedullary nail 100 includes two moving components 106, 108 that provide micromotion along the longitudinal axis of the implant 100. For example, the distal tip 106 may have an extension receivable in a central opening through the proximal body 108 to enable movement relative between the two components 106, 108 of the nail 100. As best seen in FIGS. 10A-10C, the two moving components 106, 108 may be abutted by a dynamic member 110. The dynamic member 110 may be a spring, Belville washer, polymer spacer/washer, or the like to allow controlled movement between the components 106, 108. In FIG. 10A, the dynamic member 110 is a flexible spiral cut at the proximal end of the distal tip 106. In FIG. 10B, the dynamic member 110 is a Belville washer. In FIG. 10C, the dynamic member 110 is a polymer washer. In each instance, the dynamic member 110 is configured to allow compression and contraction over the fracture site at a predetermined strain rate.

Figure 11A:
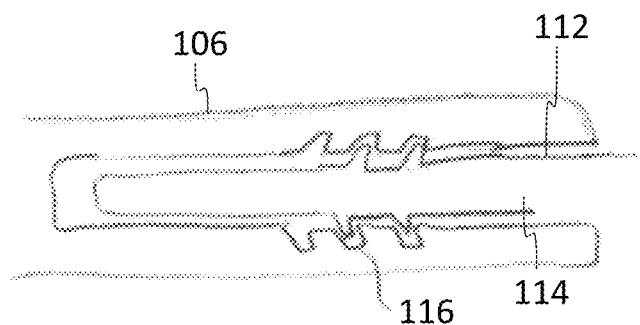
FIGS. 11A-11C illustrate alternative examples of locking movement between the moveable components of the intramedullary nail.
Figure 11B:
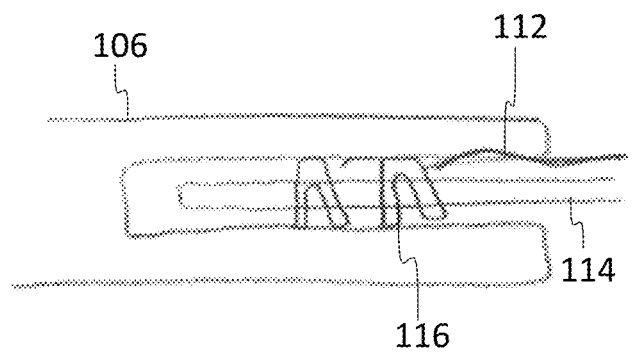
Figure 11C:
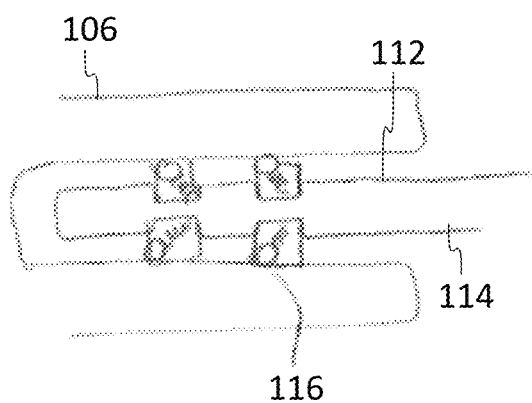

A mechanical lock 112 may be used to stop motion between the moveable components 106, 108. The mechanical lock 112 may include a central locking rod 114 extending through the proximal body 108 and into the extension of the distal tip 106. As best seen in FIGS. 11A-11C, the locking rod 114 includes a locking member 116 at its free end configured to interface with the inside of the distal tip 106. The locking member 116 may be configured to allow movement in one direction and provide locking in the opposite direction. Alternatively, the locking member 116 may prevent movement in both directions. In FIG. 11A, the locking member 116 is a ratcheting lock with a plurality of teeth configured to intermesh and prevent movement. In FIG. 11B, the locking member 116 is a caulk gun clamp. In FIG. 11C, the locking member 116 is a one way clutch. It will be appreciated that any suitable locking mechanism may be used to secure the two moveable components 106, 108 in a fixed relative position.

The locking rod 114 and locking member 116 may be actuated into position. The movement may be mechanical and/or electronic. The distal end of the locking rod 114 may connect to an actuator 118 configured to translate the locking rod 114 along the central longitudinal axis of the implant 100. In one embodiment, the implant 100 may have an internal antenna 120 such that the implant 100 may be locked post operatively with wireless communication. The wireless transmission to the implant 100 may occur through the antenna 120 and into the actuator 118. In one embodiment, the actuator 118 may be made of a shape-memory material, such as nitinol. As the power is transferred to the actuator 118, the nitinol heats and reduces length to provide a stroke. The stroke is then used to push the locking rod 114 which engages the lock 116 between the two moving components 106, 108 of the implant 100, thereby preventing them from moving relative to themselves.

The configuration of implant 100 allows the dynamization to be turned off post operatively. This allows the implant 100 to be static and rigid for callus formation to consolidate and heal. The reverse dynamization implant 100 provides for an initially passively active implant and a subsequent static implant allowing for the change to occur internally with no need to operate on the patient. In this manner, surgeons may be able to help treat patients who may be at a high risk for non-unions or athletes who need accelerated bone healing to provide treatment to allow for both.

Unless specified otherwise, the components of all of the devices disclosed herein may be manufactured of any suitable materials including metals (e.g., titanium), metal alloys (e.g., stainless steel, cobalt-chromium, cobalt-chrome-molybdenum, tungsten carbide, and titanium alloys), carbon composites, ceramics, plastics, plastic composites, or polymeric materials (e.g., polyether ether ketone (PEEK), polyethylene, ultra-high molecular weight polyethylene (UHMWPE), resorbable polylactic acid (PLA), polyglycolic acid (PGA), polyphenylene sulfone (PPSU), polysulfone (PSU), polycarbonate (PC), polyetherimide (PEI), polypropylene (PP), polyacetals, or mixtures or co-polymers thereof), and/or combinations thereof. In some embodiments, the devices may include radiolucent and/or radiopaque materials. The components can also be machined and/or manufactured using any suitable techniques (e.g., 3D printing).

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that the components of the various devices disclosed above may be combined or modified in any suitable configuration.

What is claimed is:

1. A system for reverse dynamization comprising:
an implant configured to be secured to bone, the implant having one or more moveable components creating a semi-rigid configuration to allow for micro-motion of the bone for a period of time,
wherein the one or more moveable components are changeable to a static condition creating a rigid configuration to prevent subsequent movement of the bone
wherein the one or more moveable components is a reverse dynamization component that is formed of a two-part curing material with each part housed in separate compartments separated by a barrier, and when the barrier breaks and the two-parts mix, the resulting mixture cures and stiffens.

2. The system of claim 1, wherein the implant is an expandable spinal implant, a bone plate, or an intramedullary nail.

3. The system of claim 1, wherein the one or more moveable components are locked post-operatively.

4. The system of claim 1, wherein the one or more moveable components are changed to the static condition by manipulation or activation.

5. The system of claim 1, wherein the one or more moveable components are changed to the static condition by a material property change.

6. The system of claim 1, wherein micro-motion of the bone is permitted for the first 2-6 weeks of healing.

7. An expandable implant comprising:
a front ramp having at least one ramped surface and a rear ramp having at least one ramped surface;
a central drive screw retained in the rear ramp and threadedly engaged with the front ramp;
an upper endplate and a lower endplate, each slidably engaged with the ramped surfaces of the front and rear ramps, respectively, wherein rotation of the central drive screw moves the front ramp toward the rear ramp forcing the upper and lower endplates outward, thereby expanding a height of the implant; and
a reverse dynamization component located along the central drive screw, the reverse dynamization component being flexible to provide for micro-motion for a given period of time, and subsequently, stiffens to rigidly fix the upper and lower endplates
wherein the reverse dynamization component is formed of a two-part curing material with each part housed in separate compartments separated by a barrier, and when the barrier breaks and the two-parts mix, the resulting mixture cures and stiffens.

8. The implant of claim 7, wherein the reverse dynamization component is a washer.

9. The implant of claim 7, wherein while flexible, the reverse dynamization component has an axial width that is variable in nature for the given period of time.

10. The implant of claim 9, wherein the reverse dynamization component is housed along a long axis of the central drive screw such that the axial width contributes to a total distance between the front and rear ramps.

11. The implant of claim 9, wherein a height across the upper and lower endplates change in proportion to a change in the axial width of the reverse dynamization component.

12. The implant of claim 7, wherein the reverse dynamization component is formed of a cross-linking polymer that cross-links to due to repeated strain.

13. The implant of claim 7, wherein the reverse dynamization component is a work-hardened spring that stiffens as the spring is overloaded and repeatedly deformed.

* * * * *